United States Patent
Lennox

(12) 
(10) Patent No.: US 6,537,193 B1
(45) Date of Patent: Mar. 25, 2003

(54) METHOD AND DEVICE FOR DELIVERY OF THERAPEUTIC AGENTS IN CONJUNCTION WITH ISOTOPE SEED PLACEMENT

(75) Inventor: Charles D. Lennox, Hudson, NH (US)

(73) Assignee: SciMed Life Systems, Inc., Maple Grove, MN (US)

( * ) Notice: Subject to any disclaimer, the term of this patent is extended or adjusted under 35 U.S.C. 154(b) by 75 days.

(21) Appl. No.: 09/699,675

(22) Filed: Oct. 30, 2000

Related U.S. Application Data

(63) Continuation of application No. 09/098,617, filed on Jun. 17, 1998, now Pat. No. 6,159,143.

(51) Int. Cl.[7] ............... A61N 5/00; A61K 17/43; A61M 36/00
(52) U.S. Cl. ............... 600/3; 604/891.1; 600/8
(58) Field of Search ............... 600/1–8, 29, 30; 128/898, 927; 604/890.1, 891.1

(56) References Cited

U.S. PATENT DOCUMENTS 6,159,143 A * 12/2000 Lennox ............... 600/4

* cited by examiner

Primary Examiner—Eric F. Winakur
Assistant Examiner—Nikita R Veniaminov
(74) Attorney, Agent, or Firm—Testa, Hurwitz & Thibeault, LLP

(57) ABSTRACT

An implantable cancer therapy device includes adjacent segments of a radioactive therapeutic and an adjunctive therapeutic. The segments of radioactive therapeutic and adjunctive therapeutic can be alternatively disposed in a predetermined spatial array. The implantation can be permanent or temporary. The device can be a substantially cylindrical filament or plurality of spaced radioactive seed overlaid with an adjunctive therapeutic. The device can also be a monofilament comprising an adjunctive therapeutic, the monofilament having spaced depressions for indicating length and facilitating cutting.

3 Claims, 1 Drawing Sheet

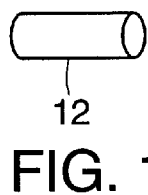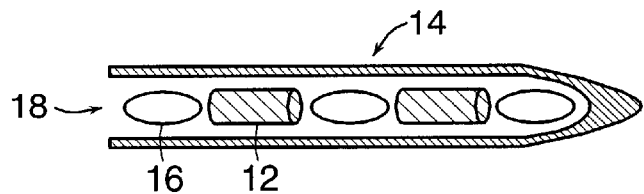
FIG. 1    FIG. 1A
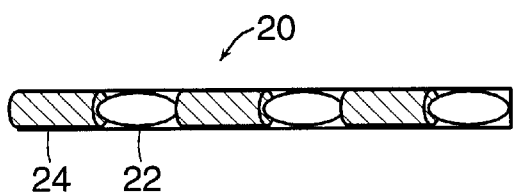
FIG. 2
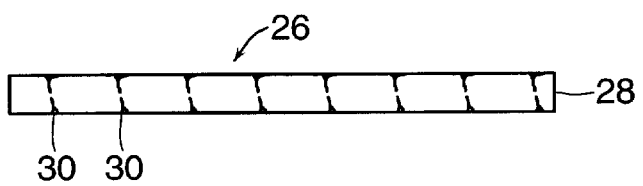
FIG. 3
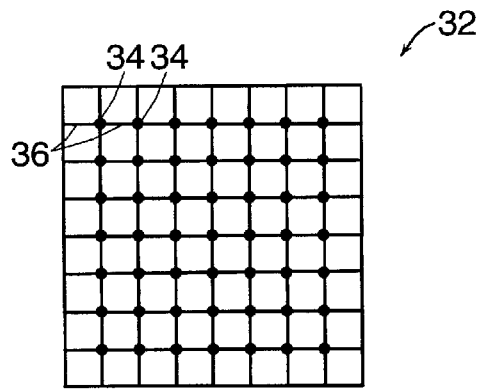
FIG. 4

METHOD AND DEVICE FOR DELIVERY OF THERAPEUTIC AGENTS IN CONJUNCTION WITH ISOTOPE SEED PLACEMENT

RELATED APPLICATIONS

This is a continuation of U.S. Ser. No. 09/098,617, filed Jun. 17, 1998 now U.S. Pat. No. 6,159,143.

TECHNICAL FIELD

This invention relates generally to the field of brachytherapy. In particular, this invention relates to brachytherapy in combination with an adjunctive therapy for the treatment of malignancy in solid organs.

BACKGROUND

Brachytherapy is a form of radiation treatment in which a radiation source is placed into or adjacent to a malignant tumor. There are two general categories of brachytherapy: high dose rate (HDR); and low dose rate (LDR). HDR brachytherapy involves the placement of a radiation source with high activity adjacent to or into the malignant tumor for a limited period of time. LDR brachytherapy involves the placement of a low activity radiation source adjacent to or into the malignant tumor for an indefinite period of time.

The radiation sources used in LDR brachytherapy are radioactive isotopes. The most common isotopes used in LDR brachytherapy are $^{103}$Pd (Palladium), $^{125}$I (Iodine), $^{198}$Au (Gold), and $^{192}$Ir (Iridium). These isotopes are packaged in a cylindrical titanium housing and are commonly referred to as isotope seeds. The typical dimensions of the seeds are 0.5 mm in diameter and 0.5–1.0 cm in length. The isotopes used in LDR brachytherapy are chosen for their low energy and short half life. Low energy provides for limited penetration of the radiation so that the radiation effect is limited to the tumor without affecting adjacent normal tissue. A short half life is desirable so that the radiation dose can be delivered in a reasonably short time frame.

For $^{103}$Pd and $^{125}$I, the zone of therapeutic effect is limited to about a 1 cm diameter sphere about the seed, so typically, a three-dimensional array of seeds is used to treat a tumor. In LDR brachytherapy of prostate cancer, over 100 seeds are typically used. Because solid tumors, such as those found in prostate cancer, are perceived to be diffuse, the entire organ is targeted.

To place multiple seeds into a three dimensional array, seeds can be delivered by needles using a two dimensional grid pattern, and longitudinal spacing. The two dimensional grid is usually defined by a needle guide, called a template. The template consists of a matrix of holes that guide the longitudinal advancement of the needles to insure their proper two dimensional position in the tumor. Once the two dimensional array of needles is established in the tumor, the seeds are deposited along the longitudinal axis of each needle. The spacing of the seeds along the longitudinal axis of the needle is accomplished by using biocompatible spacers between the seeds. The spacers and seeds are alternately inserted into the needle prior to placement of the needle into the tumor. Once the needle is placed into the tumor, a mandrel is used to maintain the position of the line of seeds and spacers as the needle is withdrawn. This leaves a line of seeds in their proper longitudinal position. This process is then repeated at the other two dimensional grid coordinates forming the desired three dimensional array of seeds.

LDR brachytherapy is an effective modality for treating localized malignancies, however, it is not always successful in eradicating the malignancy. Some tumors are resistant to the effect of radiation, and sometimes the placement of seeds is not optimal, leaving spaces that are under treated. To enhance the effectiveness of brachytherapy, adjunctive treatments are often used. These adjunctive treatments include external beam radiation therapy, hyperthermia, systemic chemotherapy, systemic hormonal therapy, and immunotherapy.

Often there is a synergistic effect between brachytherapy and the adjunctive therapy. Brachytherapy can destroy the majority of the malignant cells and injured the remaining malignant cells. The adjunctive therapy can eradicate the remaining injured cells. Alternatively, the adjunctive therapy can make the malignant cells vulnerable to the radioactive isotope from the brachytherapy, for example, by holding the cells in the radiosensitive part of the cell cycle (e.g., G2M, late G2 or G2/S). Examples of radiosensitizing agents include butyrate, gemcitabine, 5-fluorouracil, catalase, paclitaxel, and misonidazole.

SUMMARY OF THE INVENTION

This invention primarily relates to LDR brachytherapy, also referred to as permanent seed implant brachytherapy, in combination with an adjunctive therapy. In addition, the device and methods of this invention also relate to HDR brachytherapy in combination with an adjunctive therapy. As used herein, the term adjunctive therapeutic is meant to embrace materials and/or compounds that can be used to effectuate an adjunctive therapy. As used herein, the term therapeutic is meant to embrace both curative and palliative treatments.

More specifically, the invention relates to radiation therapy using methods and devices that sensitizes target pathologies to radiation without sensitizing normal non-target tissue to radiation. In this aspect, the invention involves the placement of devices containing radiation sensitizing agents into a target pathology concurrent with a radiation therapy. This invention is not specific to a particular radiation sensitizing agent. Also, the sensitizing agent can have beneficial properties in addition to sensitizing the target pathology to radiation.

In one aspect, the invention features an implantable cancer therapy device including adjacent segments of a radioactive therapeutic and an adjunctive therapeutic. The segments of radioactive therapeutic and adjunctive therapeutic can be alternatively disposed in a predetermined spatial array. The implantation can be permanent or temporary. The device can be a substantially cylindrical filament, a mesh patch, or plurality of spaced radioactive seeds overlaid with an adjunctive therapeutic.

The device can also be a monofilament comprising an adjunctive therapeutic and a radioactive therapeutic. The monofilament has spaced depressions for indicating length and facilitating cutting. The depressions can be evenly or unevenly spaced.

In another aspect, the invention features a method of treating cancer comprising the steps of placing adjacent segments of a radioactive therapeutic and an adjunctive cancer therapeutic into or adjacent to a malignant tumor. The segments can be in the form of a substantially cylindrical filament with a diameter that is smaller than the inner diameter of a brachytherapy seed placement device.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a view of the substantially cylindrical unit which contains an adjunctive therapeutic.

FIG. 1A shows a substantially cylindrical member which includes an adjunctive therapeutic placed in a needle with radioactive seeds.

FIG. 2 shows a device which comprises an integral member having alternating radioactive segments and adjunctive therapeutic segments.

FIG. 3 shows a therapy device which comprises a monofilament including adjunctive therapeutic with spaced depressions.

FIG. 4 shows a therapy device in the form a mesh patch.

DETAILED DESCRIPTION

The invention is a device, and the method of use thereof, that replaces the seed spacers currently known in the art, and which can deliver adjunctive therapeutic agents or facilitate delivery of adjunctive therapy while configuring the radioactive therapeutic and adjunctive therapeutic in a predetermined spatial array. The device includes a carrier for the radiation therapeutic and for the adjunctive therapeutic. The device can be placed into or adjacent to the target pathology by surgical or nonsurgical means.

The device can be constructed from a compound containing a bio-absorbable polymer and an adjunctive therapeutic. The device can also be constructed so that the adjunctive therapeutic can be added after the device is manufactured.

For effective coverage of the target pathology, the device can be placed into the target tissue in a three-dimensional array. In those embodiments in which the device is either a pellet or a filament, it can be delivered by needles using a two-dimensional grid pattern and longitudinal spacing. The two-dimensional grid is usually defined by a needle guide, called a template. The template consists of a matrix of holes that guide the longitudinal advancement of the needles to ensure their proper two-dimensional position in the tumor. Once the two-dimensional array of needles is established in the tumor, the seeds are deposited along the longitudinal axis of each needle. The spacing of the seeds along the longitudinal axis of the needle is accomplished by using biodegradable spacers between the seeds. The spacers and seeds are alternately inserted into the needle prior to placement of the needle into the tumor. Once the needle is placed into the tumor, a mandrel is used to maintain the position of the line of seeds and spacers as the needle is withdrawn. This leaves a line of seeds in their proper longitudinal position. This process is then repeated at the other two-dimensional grid coordinates forming the desired three-dimensional array of seeds. Alternatively, a two-dimensional array can be created by weaving radioactive therapeutic and adjunctive therapeutic into a mesh patch. Such a patch can be applied intracavitarily, although it can also be applied interstitially.

The adjunctive therapeutic carried by the device can include chemotherapeutic agents, hormones, hormone agonists, gene vectors, vaccines, and monoclonal antibodies. The device can also be constructed to provide therapy by generation of heat by absorption of externally applied alternating electromagnetic fields.

Referring to FIG. 1, in one embodiment, a therapy device comprises a substantially cylindrical unit 12 including an adjunctive therapeutic agent. The dimensions can be 0.5 mm in diameter and 0.5–1.0 cm in length. The dimensions of the substantially cylindrical unit 12 can vary so long as the length of the device provides for proper spacing of a plurality of brachytherapy seeds 16 (FIG. 1A), and the diameter of the device is suitable to accommodate the inner diameter of the seed placement device 14 (FIG. 1A). With reference to FIG. 1A, one method for delivery of a therapy device 18 is by percutaneously placing a needle 14 into the pathology under image guidance, and inserting the device into the pathology through the needle. The device 18, which includes alternating segments of an adjunctive therapeutic agent 12 and brachytherapy seeds 16 pass through the needle 14 into the pathology. A single device or a spatial array of devices can be placed into the pathology in this manner.

Referring to FIG. 2, in another embodiment, the therapy device 20 comprises an integral unit strip with alternating radioactive sections 22 and adjunctive therapeutic segments 24. In another embodiment, shown in FIG. 3, the therapy device 26 comprises an elongated member (or monofilament) 28 including an adjunctive therapeutic. The diameter of the monofilament can be suitable to accommodate the inner diameter of a seed placement device (not shown). The length of the monofilament 28 can be at least a length for spacing of the brachytherapy seeds. In this embodiment, the monofilament 28 can be trimmed to create custom spacers for a particular treatment regime. The monofilament can include spaced depressions 30 for indicating length and facilitating cutting or breaking off segments of predetermined size.

Referring to FIG. 4, in another embodiment, the therapy device 32 can be in the form of a mesh patch with radioactive therapeutic 34 and adjunctive therapeutic 36 placed in a predetermined array. In yet another embodiment, the device can be a composite structure comprising an outer shell and an inner structure which includes the adjunctive therapeutic (not shown). The outer shell can be biodegradable so as to release the therapeutic agent in the inner structure or can be porous to allow the therapeutic agent in the inner structure to escape.

The material and construction of the device is determined by the requirements of the adjunctive therapeutic to be delivered. The adjunctive therapeutic can be incorporated into the device at the time of manufacture, or at the time of surgery. The device can be absorbed by the body over time, and use such property to release the adjunctive therapeutic, or the device can remain in the body and release the adjunctive therapeutic by other means for example, an osmotic pump, bioerosion, bioabsorption or diffusion. The device can remain in the target pathology indefinitely, where it can be absorbed by the body or discharged from the body. Alternatively, the device can be manually removed from the body.

In any of the forgoing embodiments, the adjunctive therapeutic segment and/or the radioactive segment can have a ferrous component to allow for induced heating from an external alternating electromagnetic field. Materials to construct said device are well known in the art.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An elongated monofilament for use with a branchytherapy seed placement device, said monofilament comprising an adjunctive therapeutic and having a diameter that is smaller than the inner diameter of the brachytherapy seed placement device and is capable of being trimmed for use as a brachytherapy seed spacer.

2. The monofilament of claim 1, having spaced depressions for indicating length and facilitating cutting.

3. The monofilament of claim 2, wherein said depressions are evenly spaced.

* * * * *